United States Patent [19]  [11] 3,957,891
Gelfand  [45] May 18, 1976

[54] SUBSTITUTED ALPHA, BETA-DICHLOROSTYRENES

[75] Inventor: Samuel Gelfand, Niagara Falls, N.Y.

[73] Assignee: Hooker Chemicals & Plastics Corporation, Niagara Falls, N.Y.

[22] Filed: Sept. 28, 1973

[21] Appl. No.: 401,768

[52] U.S. Cl. .............................. 260/651 R; 71/107; 260/488 R; 260/488 CD; 260/515 A
[51] Int. Cl.² .......................................... C07C 25/28
[58] Field of Search......... 260/651 R, 651 F, 650 R, 260/650 F

[56] References Cited
UNITED STATES PATENTS

| | | | |
|---|---|---|---|
| 2,745,884 | 5/1956 | Kundiger et al. | 260/650 R |
| 2,813,132 | 11/1957 | Kundiger et al. | 260/650 R |
| 2,830,096 | 4/1958 | Lane | 260/650 R |
| 3,134,808 | 5/1964 | Weil et al. | 260/521 H |

OTHER PUBLICATIONS
Kunckell et al., Ber. 33, pp. 2654–2657, 1900.

Kunckell, Chem. Abs. 7, 2388⁷⁻⁹, 2389, 1913.

Newman et al., J.A.C.S., 72, 4002–4003, 1950.

Primary Examiner—Howard T. Mars
Attorney, Agent, or Firm—Peter F. Casella; William J. Crossetta, Jr.

[57] ABSTRACT

New compounds and a process for the preparation thereof are disclosed of the formula:

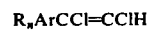

$R_nArCCl=CClH$ wherein Ar is an aromatic nucleus, aromatic being defined herein as a derivative of benzene, each R is independently selected from halogen, alkyl and haloalkyl and n is an integer from 2 to 4. The above compounds are useful as chemical intermediates for the preparation of compounds having herbicidal activity.

4 Claims, No Drawings

SUBSTITUTED ALPHA, BETA-DICHLOROSTYRENES

BACKGROUND OF THE INVENTION

In recent years, the development of selective herbicidal compounds has become of increasing commercial importance. Of particular importance is the development of ring and side chain halogenated phenylacetic acids, as they have been shown to have a particularly effective control of certain non-desirable weeds. U.S. Pat. No. 3,134,808 discloses several examples of chlorine substituted phenylacetic acids and their use as herbicides. A problem with the commercialization of these compounds has been, however, the expense of commercial preparation thereof and the attendant difficulties inherent in the known commercial processes for their preparation. Among the methods which have been advanced for the preparation of these compounds has been the chlorination of trihalophenylacetic acids, in the molten state, or, in an organic solvent resistant to halogenation; or, alternately by the chlorination of the corresponding substituted phenylacetonitrile to introduce chlorine atoms as desired into the alpha-position, followed by the controlled hydrolysis of the nitrile to the acid. Such methods, however, are complex and difficult to control and result in low yield products which are expensive to reproduce.

It is an object of the instant invention to provide useful intermediates for the preparation of substituted phenylacetic acids. It is also an object of this invention to produce a process for the production of substituted phenylacetic acids in high yields and high purity. Further, it is an object of the instant invention to provide a process for the preparation of intermediates useful in the production of substituted phenylacetic acids. It is still another object of this invention to provide a simple process for the production of substituted phenylacetic acid. These and other objects will become more apparent from the following discussion.

SUMMARY OF THE INVENTION

In accordance with this invention, new compounds of the formula:

$$R_nArCCl=CClH$$

wherein Ar is an aromatic nucleus, aromatic being defined herein as a derivative of benzene, each R is independently selected from the group consisting of halogen, alkyl and haloalkyl, and $n$ is an integer from 2 to 4 are prepared by a process which comprises reacting a substituted aromatic of the formula:

$$R_nAr$$

wherein $R_n$ and Ar are as hereinbefore defined and having unsubstitution at two adjacent ring positions with trichloroethylene in the presence of a Friedel-Crafts catalyst, the reaction being set out wherein Ar is benzene as follows:

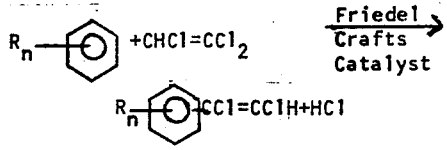

The product of this reaction can be further reacted with an alcohol in the presence of a strong base to produce the substituted phenyl alkyl acetate, which in turn can be hydrolyzed and readily alpha-chlorinated to produce the substituted phenylacetic acid.

Illustrative of the substituted aromatic compounds, which may be utilized as halo-aromatic reactants in the process of the present invention, generally containing from 6 to 14 carbon atoms are: 2,4-dichlorotoluene, 3,4-dichlorotoluene, 2,5-dichlorotoluene, 2-chloro-p-xylene, 4-chloro-o-xylene, p-dibromobenzene, p-chlorobromobenzene, 2,4-dibromotoluene, 2,4-dichloroethyl benzene, p-chloro-fluoro benzene, p-chlorobenzyl chloride, 2,4-dichlorobenzyl chloride ortho-dichlorobenzene, meta-dichlorobenzene, para-dichlorobenzene, 1,2,3-trichlorobenzene, 1,2,4-trichlorobenzene, 1,2,3,4-tetrachlorobenzene, and the like. Other substituted aromatic hydrocarbons of the type described herein which will not adversely affect the reaction mechanism can be employed. Illustrative examples of the Friedel-Crafts catalyst which are operable in the instant invention are aluminum chloride and aluminum bromide. Only a catalytic amount is required, generally such being in the range of about 0.01% to about 10% by weight of reactants with the preferred range being about 0.1 to about 2% by weight.

The reaction is generally accomplished by heating the reactants in the presence of the Friedel-Crafts catalyst until the reaction is complete as evidenced by the evolution of the required amount of hydrogen halide. The reaction temperature will vary with the type of catalyst being employed and the reactivity of the reactants but generally has a range of about 50°C to about 200°C with a preferred range being from about 60°C to about 135°C. For aluminum chloride, the temperature will generally be in the range of about 50°C to about 150°C.

A solvent is not generally necessary to produce the compounds of the instant invention but one can be used to moderate or facilitate the reaction. Among the solvents which can be used are perchloroethylene, carbon tetrachloride, octachlorocyclopentene, acetylene tetrachloride, and the like. Other solvents of higher boiling point which maintain the required reaction temperature and do not react with either of the selected reactants or the catalysts to adversely affect the reaction mixture can also be employed. The use of solvents, such as perchloroethylene or carbon tetrachloride, will usually require a higher operating temperature. Thus, for any particular reaction, the temperature selected will generally depend upon the catalyst, the solvent, and the reactivity of reactants.

The reaction product is isolated by methods known in the art, e.g., in the case of liquid products, the catalyst is removed by washing with aqueous hydrochloric acid, and the product is isolated by distillation.

In order that those skilled in the art may better understand the present invention and the manner in which it may be practiced, the following illustrative examples are given.

In the specification, examples and claims, parts are by weight and temperatures are in degrees centigrade, unless otherwise stated.

EXAMPLE 1 — PREPARATION OF 2,4,5,α-β-PENTACHLOROSTYRENE

A mixture containing 99.5 g (0.5 mole), of 1,2,4-trichlorobenzene, 32.9 g (0.25 mole) of trichloroethylene and 10 g of aluminum chloride was heated and stirred at 80°–90°C for 3 hours, during which 0.5 mole of hydrogen chloride was evolved. The product was washed to remove catalyst and after drying, the crude product was recovered by distillation at reduced pressure and further purified by recrystallization from ethanol, m.p. 78°–79°C (uncorrected).

| Analysis for $C_8H_3Cl_5$: Percent | Theoretical | Found |
|---|---|---|
| Carbon | 34.76 | 34.54 |
| Hydrogen | 1.09 | 1.03 |
| Chlorine | 64.1 | 63.8 |

The product was identified as α,β-2,4,5-pentachlorostyrene by comparison of the Proton Magnetic Resonance Spectrum with that of known compounds:

NMR Shifts
(ppm from Tetramethylsilane)

ArCHhd a=C / Hb

| | Ha | Hb |
|---|---|---|
| β,β-Dichlorostyrene | 6.78 | — |
| Trans-β- Chlorostyrene | 6.78 | 6.48 |
| 2,4,5-α,β-Pentachlorostyrene | — | 6.50 |

EXAMPLE 2 — PREPARATION OF 2-METHYL-4,5,α,β-TETRACHLOROSTYRENE

A mixture containing 131.5 g (1.0 mole), of trichloroethylene, 80.5 (0.5 mole) of 3,4-dichlorotoluene and 5 g. of aluminum chloride was stirred and heated at reflux for 2 hours. The reaction mixture was then washed with concentrated HCl, then with water until neutral, dried and distilled. 42.7 grams of product was collected, having a boiling point of 97°–102°C at 0.5 mm Hg pressure.

| Analysis for $C_9H_6Cl_4$: | Theoretical | Found |
|---|---|---|
| % Chlorine | 55.4 | 56.1 |

The product was further identified as a mixture of cis and trans isomers of 2-methyl-4,5,α,β-tetrachlorostyrene by proton NMR spectroscopy.

EXAMPLE 3 — PREPARATION OF 5-METHYL-2,4,α,β-TETRACHLOROSTYRENE

A mixture containing 111 g (0.689 mole), of 2,4-dichlorotoluene, 136 g (1.03 mole) of trichloroethylene and 10 g of aluminum chloride was reacted as in Example 2. The product had a boiling point of 89°–92°C at 0.15 mm Hg pressure, and was identified by elemental analysis and Proton NMR as a mixture of the cis and trans isomers of 5-methyl-2,4,α,β-tetrachlorostyrene.

EXAMPLE 4 — PREPARATION OF ETHYL 2,4,5-TRICHLOROPHENYLACETATE

A mixture containing 7.9 g (0.028 mole) of 2,4,5-α,β-pentachlorostyrene and 5.6 g potassium hydroxide in 75 ml of ethanol was stirred at reflux for 8 hours. The reaction mixture was diluted with water and extracted three times with benzene. The benzene extracts were dried, the benzene stripped, and the residue fractionated at reduced pressure. Ethyl 2,4,5-trichlorophenylacetate, identified by proton magnetic resonance spectrum, was obtained in 60% yield along with some recovered starting material.

EXAMPLE 5 - 2,4,5-TRICHLOROPHENYL ACETIC ACID

Ethyl 2,4,5-trichlorophenyl acetate (0.1 mole) in 200 ml. of aqueous 10% potassium hydroxide was heated and stirred until it went into solution. The reaction mixture was cooled to room temperature and acidified with concentrated hydrochloric acid. The 2,4,5-trichlorophenyl acetic acid which precipitated waS isolated by filtration, washed with water and dried.

I claim:
1. 2,4,5,α,β -pentachlorostyrene.
2. 2-methyl-4,5,α,β-tetrachlorostyrene.
3. 2,5,α,β tetrachlorostyrene.
4. A process for preparing compounds of the formula $R_nArCCl=CClH$ wherein Ar is benzene, and each R is independently selected from the group consisting of alkyl, halogen and haloalkyl, wherein the halogen is chlorine, bromine or fluorine and n is an integer from 2 to 4, comprising reacting a substituted benzene of the formula $R_nAr$, wherein R, n and Ar are as before described, with trichloroethylene in the presence of from about 0.01% to about 10% by weight of Friedel-Crafts catalyst selected from the group consisting of aluminum chloride and aluminum bromide, at a temperature of from about 50°C to about 200°C and in the presence of solvent selected from the group consisting of perchloroethylene, carbon tetrachloride, octachlorocyclopentene and acetylene tetrachloride.

* * * * *